United States Patent [19]

Pharis et al.

[11] Patent Number: 5,085,683
[45] Date of Patent: *Feb. 4, 1992

[54] PROMOTION OF FLOWERING OF FRUIT TREES

[76] Inventors: Richard P. Pharis, Plant Physiology Research Group, Biology Dept., University of Calgary, Calgary, Alberta, Canada, T2N 1N4; Norman E. Looney, Pomology & Viticulture Section, Agriculture Canada Research Station, Summerland, B.C., Canada, V0H 1Z0; Lewis N. Mander, Research School of Chemistry, Australia National University, P.O. Box 4,, Canberra, A.C.T. 2600, Australia

[*] Notice: The portion of the term of this patent subsequent to Jul. 17, 2007 has been disclaimed.

[21] Appl. No.: 531,614

[22] Filed: Jun. 1, 1990

Related U.S. Application Data

[63] Continuation of Ser. No. 220,382, Jul. 12, 1988, Pat. No. 4,941,908, which is a continuation of Ser. No. 824,875, Jan. 31, 1986, abandoned.

[30] Foreign Application Priority Data

Jan. 31, 1985 [GB] United Kingdom ............... 8502424

[51] Int. Cl.$^5$ ............................................. A01N 45/00
[52] U.S. Cl. ................................. 71/89; 71/DIG. 1
[58] Field of Search ............................................. 71/89

[56] References Cited

U.S. PATENT DOCUMENTS

| | | | |
|---|---|---|---|
| 3,038,794 | 6/1962 | Geary et al. | 71/89 |
| 3,830,643 | 8/1974 | Schneider et al. | 71/89 |
| 4,110,102 | 8/1978 | Pharis | 71/89 |
| 4,156,684 | 5/1979 | Crutcher | 71/89 |
| 4,242,120 | 12/1980 | Manankor | 71/89 |

FOREIGN PATENT DOCUMENTS

| | | | |
|---|---|---|---|
| 7903342 | 9/1979 | France | 71/89 |
| 0704526 | 12/1979 | U.S.S.R. | 71/89 |

OTHER PUBLICATIONS

Guttridge, C. G. Nature, vol. 196, Dec. 8, 1962.
Dennis et al., Proc. Amer. Soc. Hort. Sci., vol. 88, Jun. 1966, pp. 14-24.
Ed. Luckwill & Cutting., Physiology of Tree Crops. Mar. 25-28, 1969.
Marino and Greene, J. Amer. Soc. Hort. Sci., 106(5):593-596.
Tromp, J., J. Hort. Sci., vol. 57, No. 3, 1982, pp. 277-282.
Looney, N. E. et al., Acta Hort., 80, 1978.
Tromp, J., J. Hort. Sci., vol. 62, No. 4, pp. 433-440.
Knight, J. N. et al., Acta Horticulturae 179, 1986.
Looney et al., "Promotion of Flowering in Apple, etc.," Chem. Abstr. 104:64082b (1986) from Planta (1985).
Tompsett et al., "Promotion of Flowering, etc.," Chem. Abstr. 90:118175x (1979).
Brix et al., "Flowering Response of Western Hemlock, etc.," Chem. Abstr. 96:176035m (1982).
Pal et al., "*Endogenous Gilberellins* of Mango, etc.," Chem. Abst. 90:51472w (1979).
Stolp et al., "Abscisic Acid and the Accumulation, etc." Chem. Abstr. 87:164295x (1977).

*Primary Examiner*—Richard L. Raymond
*Assistant Examiner*—B. Bembenick
*Attorney, Agent, or Firm*—Browdy and Neimark

[57] ABSTRACT

The flowering of broad-leaved trees particularly fruit trees is promoted by applying a selected rapidly metabolizable gibberellin. Use of the method of the invention can promote return flowering and prevent biennial bearing.

13 Claims, No Drawings

PROMOTION OF FLOWERING OF FRUIT TREES

This is a continuation of application Ser. No. 220,382 filed July 12, 1988 (now U.S. Pat. No. 4,941,9 itself a continuation of earlier application Ser. No. 824,875 filed on Jan. 31, 1986, the latter abandoned without prejudice in favor of Ser. No. 07/220,382.

This invention relates to a method of promoting flowering of broadleaved trees, particularly so as to overcome problems of irregular cropping, and most notably the horticultural problem commonly referred to as 'biennial bearing' and to a composition for use in such method.

Biennial bearing is a considerable problem with a number of woody angiosperms including apple, apricot, pistachio, pecan, coffee and several species of citrus. It can result in a glut of fruit in one year and very low production the next. The low crop in the "off" year is directly related to the failure by the plant to produce an adequate number of flowers on spur shoots, or on branches bearing fruit the previous season. If the tendency toward biennial bearing is not too severe, the problem can be controlled by the use of growth retardants, ethylene generating chemicals, girdling, and the aggressive use of manual or chemical 'thinning' procedures to reduce the crop in the 'on' year. However, severe biennial bearing cannot be corrected by such procedures.

It has now been found that field applications of carefully selected gibberellins can promote 'return flowering'.

This discovery is particularly surprising because some other horticultural treatments involving gibberellins (i.e. treatments to promote fruit set or improve aspects of fruit quality) often antagonize the next year's flowering.

Thus according to the present invention there is provided a method of promoting flowering of a woody angiosperm that is prone to severe biennality which comprises applying an effective amount of rapidly metabolizable gibberellin. It is preferred to apply a gibberellin native to the species (or an analogue of such a gibberellin), and one that is metabolized so rapidly that no unwanted morphogenic side effects, such as lengthening of the plastochron, are produced. Especially suitable gibberellins are those which are hydroxylated at positions in the gibberellane skeleton other than at positions 1 and 2 and/or 1,2-dihydro. Examples of such gibberellins include gibberellin $A_4$ ($GA_4$) and its salts and esters, the C-3 epimer of $GA_4$ and its salts and esters and gibberellin $GA_1$, and its salts and esters. Examples of suitable salts and esters include the sodium salt and $C_{1-4}$ carboxylic acid esters.

The gibberellins used in accordance with the present invention may be applied with other plant growth regulators, i.e. chemical thinning agents and growth retardants, but gibberellins with persistent biological activity, especially gibberellins $A_3$ and $A_7$ should not be used. Thus, the gibberellins used in accordance with the invention should be substantially free of those gibberellins with persistent biological activity.

Although the method of the invention may be carried out on trees which are not flowering or have not flowered (e.g. to promote flowering of juvenile trees), it would normally be carried out during a season in which flowering and fruiting has already taken place, so as to stimulate 'return flowering'. The intent is to counteract or over-ride any inhibitory effect caused by the current season's flowering and/or cropping.

The application of gibberellin in accordance with the invention is desirably carried out in late spring/early summer and, depending on the crop, probably not later than about 12 weeks after anthesis. Good results have been obtained with application of gibberellin in the period from 2 to 8 weeks after anthesis on apple. Although multiple application of gibberellin may be made, significantly improved flowering has been achieved with a single application.

The method of application of gibberellin is not thought to be particularly critical and may be accomplished by spraying the gibberellin to whole trees together with a suitable carrier. The addition of conventional adjuvants such as wetting agents and dispersants may prove to be beneficial in some agronomic situations.

Only small quantities of gibberellin need be applied in order to stimulate return flowering in accordance with the invention. Satisfactory results have been achieved with as little as 3 µg per spur and it is expected that solutions containing as little as 30 ppm of the gibberellin will give satisfactory results when applied as foliar sprays. Normally the method of invention involves the use of a gibberellin as the sole plant growth modifying agent but the addition of a natural cytokinin, zeatin, appeared to enhance the flower promoting activity in one experiment (even though previous tests by us of this and other cytokinins alone had not been encouraging). Thus, the method cannot rule out the possibility that the addition of other plant growth regulators might enhance activity.

Compositions for use in accordance with the method of the invention comprising a rapidly metabolizable gibberellin, together with a horticulturally acceptable diluent or carrier, said compositions being substantially free of gibberellins with persistent biological activity, are novel and form a further aspect of the invention.

The invention described here has great potential for improving the cropping behaviour of fruit trees prone to biennial flowering and its success is particularly surprising since the weight of experimental evidence would predict the opposite. The method of the invention as applied to apple trees will now be described in the following examples.

EXAMPLE ONE

Plant material and cultural conditions

Nine mature (21-year-old) spur-type Golden Delicious apple trees with a history of severe biennial bearing were selected during the 1982 blossom period from a larger population of trees in Orchard 1C of the Summerland, British Columbia, Canada Research Station. Each tree was judged to be 'on' in 1982, with virtually every spur flowering. Thus, return flowering in 1983 was expected to be very low.

To improve the chances of return flowering each tree was carefully hand-thinned within 2 weeks of full bloom. Eighty percent of the flowering spurs were defruited and a single fruit retained on the remaining spurs. These trees received normal cultural attention during the 1982 growing season and the fruit was harvested in mid-October. Care was taken during the harvest and pruning operations during dormancy to avoid removing or damaging treated spurs and branches.

Growth regulator applications

The following treatment solutions were applied with a small paint brush to 2 fully expanded rosette leaves on each of 25 defruited spurs randomly located throughout each of the 9 trees;

a) 60% ethanol control;
b) 2 ppm $GA_4$* in 60% ethanol;
c) 20 ppm $GA_4$* in 60% ethanol;
d) 200 ppm $GA_4$* in 60% ethanol;
e) 20 ppm $GA_4$* plus 20 ppm zeatin in 60% ethanol.

*The $GA_4$ used contained approx. 5% GA7 and was purchased from Abbott Lab., Chemicals and Agricultural Products Div., N. Chicago, Ill., U.S.A.

Each of these treatments was applied during the period of June 14–17, 1982, or about 4.5 weeks after full bloom. Treatments b) to e) were applied to additional spurs on the same trees on June 30, or about 7 weeks after full bloom.

Each leaf was 'painted' on all surfaces, applying about 1.5 ml of solution to each spur. Thus, the amount of $GA_4$ applied ranged from 0 to approximately 300 $\mu g$ per spur. Treatment e) applied 30 ug of $GA_4$ and 30 ug of zeatin.

Measurements and statistical analysis

Early in the bloom period of 1983 each spur was examined for the presence or absence of flowers. There were no apparent differences in the number or 'quality' of individual flowers per cluster so no detailed measurements of this nature were made. The flowering results (expressed as a percentage of flowering spurs per treatment per tree) were subjected to an analysis of variance of 9 treatments and 9 blocks (trees).

The 200 ppm $GA_4$ treatment, applied at either 4.5 or 7 weeks after anthesis in 1982, significantly increased the proportion of spurs that produced flowers in 1983 (Table 1). Furthermore, flowering was increased by 3 of the 4 treatments involving 20 ppm $GA_4$, and the $GA_4$ plus zeatin mixture appeared to be superior to $GA_4$ alone. The 2 ppm treatment applied 7 weeks after bloom was ineffective and the relatively high value resulting from the comparable 4.5 week treatment, although statistically significant, may be anomalous.

The amount of return flowering obtained with the 200 ppm $GA_4$ treatments would be enough to insure a commercial crop of apples given reasonable conditions for fruit set and development. This treatment would, therefore, be of considerable commercial interest.

However, of particular biological significance is that, contrary to previous results with exogenously applied gibberellins $A_3$, $A_7$ and $A_4$ plus $A_7$ mixtures, gibberellin $A_4$ significantly promoted flowering relative to an appropriate control treatment.

TABLE 1

The effect (as a % of flowering spurs) of $GA_4$ and $GA_4$ plus zeatin treatments (applied to defruited Golden Delicious spurs in 1982) on return flowering of those spurs in 1983.

| Treatment Concentration (mg $l^{-1}$) | | Treatment time* | |
|---|---|---|---|
| | | 4.5 weeks | 7 weeks |
| Control | 0 | $2.27^{a**}$ | |
| $GA_4$ | 2 | $7.74^b$ | $2.37^a$ |
| $GA_4$ | 20 | $6.21^b$ | $3.95^{ab}$ |
| $GA_4$ + Zeatin | 20 | $8.22^b$ | $6.82^b$ |
| $GA_4$ | 200 | $12.67^c$ | $13.71^c$ |

*Weeks after full bloom in 1982.
**Mean Values followed by differing letter are statistically significant at $P \leq 0.05$ using Duncan's Multiple Range Test (S.E. of the mean = 1.37).

EXAMPLE TWO

Plant material and cultural conditions

Five 16-year-old Golden Delicious apple trees exhibiting severe biennial bearing were selected from a larger population of trees in Orchard 1C of the Summerland, British Columbia Research Station. 1978 was the 'on' year for these trees and to improve the chances of obtaining a crop in the following year they were severely hand-thinned at 20 days after full bloom. On average, 19 of each 20 flowering spurs were defruited at that time.

Growth regulator applications

At 22 days after full bloom 60 defruited spurs were selected and tagged on each tree, and one of the following treatments was applied to 20 spurs per tree:

a) 60% ethanol control;
b) 25 ug of C-3-epi-$GA_4$ in 60% ethanol; and
c) 50 ug of C-3-epi-$GA_4$ in 60% ethanol.

Each treatment was applied in approximately 250 $\mu l$ of solution applied as a fine aerosol spray to the spur rosette leaves and bourse shoot. Adjacent spurs were protected from the treatment.

Measurement and statistical analysis

Each spur that could be located (a few spurs were lost during the 1978–79 dormant period) was examined in early May of 1979 for the presence of blossoms. The number of flowers in each blossom cluster was also recorded. The results were expressed as the percentage of treated spurs exhibiting flowers on each tree, and these values were analyzed with an analysis of variance of 3 treatments and 5 blocks.

Spurs treated with C-3-epi-$GA_4$ were significantly more likely to differentiate flowers than the ethanol-treated control (Table 2). Furthermore, the response was related to the concentration of C-3 epi-$GA_4$ applied; 50 ug per spur being significantly more effective than the 25 ug C-3 epi-$GA_4$ treatment. There was no significant treatment effect on the number of flowers per flowering cluster, with the average values for treatments a) to c) being 5.1, 5.24 and 5.22, respectively.

TABLE 2

The effect of C-3 epi-$GA_4$ (applied to defruited Golden Delicious apple spurs 22 days after full bloom in 1978) on the percentage of spurs flowering in 1979.

| Treatment | Return flowering (%) |
|---|---|
| a) Control (250 $\mu l$ of 60% ethanol) | $29.6^{a*}$ |
| b) 25 ug C-3 epi-$GA_4$ in 250 ul of 60% ethanol | $35.8^b$ |
| c) 50 ug C-3 epi-$GA_4$ in 250 ul of 60% ethanol | $52.8^c$ |

*Mean values followed by different letters differ significantly at $P \leq 0.05$. (S.E. of the mean = 4.63).

The significance of these findings is that even where the tendency of the trees was to initiate a rather high number of flowers (nearly 30% of the control spurs exhibited flowers compared to about 2% in Example 1) a significant promotive effect of the gibberellin treatment was apparent. Furthermore, the method of application differed from Example 1 in that more of the spur leaves were treated and the material was applied in a low volume aerosol spray.

EXAMPLE THREE

Experiments as described in Examples 1 and 2 were carried out to assess the effects on return flowering of $GA_4$ and $GA_1$ C-13-acetate applied at two concentrations. Statistical comparisons were made between trees with high and low return flowing in 1985 and between spurs which were with and without fruit in 1984. The results are shown in the following Tables 3 to 5.

TABLE 3

Percentage of flowering on spurs with fruit in 1984. Trees with low return flowering in 1985.

| Treatment | Tree No. | | | | | |
|---|---|---|---|---|---|---|
| | 29-3 | 29-4 | 29-5 | 29-21 | 29-23 | $\bar{X}_5$ |
| No spray | 0.0 | 0.0 | 0.0 | 4.2 | 0.0 | 0.8b |
| 5 ppm $GA_4$ | 7.3 | 0.0 | 0.0 | 2.9 | 3.3 | 2.7b |
| 50 ppm $GA_4$ | 3.8 | 7.3 | 0.0 | 4.5 | 2.8 | 3.7b |
| 5 ppm $GA_1$ C-13-acetate | 2.0 | 3.3 | 0.0 | 2.5 | 0.0 | 1.6b |
| 50 ppm $GA_1$ C-13 acetate | 13.3 | 9.4 | 6.3 | 6.9 | 2.2 | 7.6a | a, b = treatments with differing letters are statistically significantly different at $P \leq 0.05$ by Duncan's Multiple Range test

TABLE 4

Percentage of flowering in 1985 on spurs with fruit in 1984. Trees with high and low return flowering combined to calculate the $\bar{X}_{10}$.

| Treatment | Tree No. | | | | | | | | | | |
|---|---|---|---|---|---|---|---|---|---|---|---|
| | 29-1 | 29-2 | 29-7 | 29-8 | 29-22 | 29-3 | 29-4 | 29-5 | 29-21 | 29-23 | $\bar{X}_{10}$ |
| No spray | 0.0 | 7.7 | 28.6 | 4.2 | 13.6 | 0.0 | 0.0 | 0.0 | 4.2 | 0.0 | 5.8b |
| 5 ppm $GA_4$ | 13.0 | 7.1 | 12.0 | 25.0 | 26.1 | 7.3 | 0.0 | 0.0 | 2.9 | 3.3 | 9.7a |
| 50 ppm $GA_4$ | 16.7 | 0.0 | 12.1 | 28.6 | 22.2 | 3.8 | 7.3 | 0.0 | 4.5 | 2.8 | 9.8a |
| 5 ppm $GA_1$ C-13-acetate | 14.3 | 17.8 | 43.6 | 30.4 | 20.0 | 2.0 | 3.3 | 0.0 | 2.5 | 0.0 | 13.4a |
| 50 ppm $GA_1$ C-13-acetate | 20.8 | 10.0 | 15.8 | 29.4 | 48.1 | 13.3 | 9.4 | 6.3 | 6.9 | 2.2 | 16.2a | a, b = treatments with differing letters are statistically significantly different at $P \leq 0.05$ by Duncan's Multiple Range test

TABLE 5

Percentage of flowering (spurs with fruit in 1984 combined with spurs that had no fruit in 1984) for trees with low return flowering in 1985.

| Treatment | Tree No. | | | | | |
|---|---|---|---|---|---|---|
| | 29-3 | 29-4 | 29-5 | 29-21 | 29-23 | $\bar{X}_5$ |
| No spray | 2.5 | 0.0 | 0.5 | 2.1 | 0.5 | 1.2c |
| 5 ppm $GA_4$ | 4.8 | 1.6 | 3.2 | 5.0 | 3.3 | 3.6b |
| 50 ppm $GA_4$ | 2.6 | 4.4 | 1.3 | 2.6 | 1.9 | 2.6bc |
| 5 ppm $GA_1$ C-13-acetate | 2.6 | 3.2 | 1.4 | 2.7 | 0.8 | 2.1bc |
| 50 ppm $GA_1$ C-13 acetate | 7.8 | 6.8 | 8.3 | 4.7 | 1.4 | 5.8a | a, b, c = treatments with differing letters are statistically significantly different at $P \leq 0.05$ by Duncan's Multiple Range test

We claim:

1. A method of promoting flowering of a fruit or nut bearing woody angiosperm which comprises applying to said woody angiosperm, as a foliar treatment, a flower promoting effective amount of a rapidly metabolized gibberellin, said gibberellin being applied in the substantial absence of gibberellins $A_3$ and $A_7$.

2. A method according to claim 1 wherein the gibberellin is hydroxylated other than at positions 1 and 2.

3. A method according to claim 1 wherein the gibberellin is C-1,2-dihydro.

4. A method according to claim 1 wherein the gibberellin is gibberellin $A_1$, gibberellin $A_4$, C-3 epi-gibberellin $A_4$ or a salt or ester of any of said gibberellins.

5. A method according to claim 4 wherein the gibberellin is gibberellin $A_1$ or a salt or ester thereof.

6. A method according to claim 4 wherein the ester is a $C_{1-4}$ carboxylic acid ester.

7. A method according to claim 1 wherein the woody angiosperm is an apricot, pear, citrus, pistachio, pecan, coffee or any other fruit or nut bearing angiosperm tree species or variety with a demonstrated history of poor flowering and/or flowering of a periodic and/or biennial nature.

8. A method of promoting flowering according to claim 1 wherein the gibberellin is applied during the period when normal floral induction, initiation, differentiation and development, occurs.

9. A method according to claim 1 wherein the gibberellin is applied during the spring or summer preceding the year in which increased flowering is desired.

10. A method according to claim 1 wherein the gibberellin is applied not more than 12 weeks after flowering or not more than 12 weeks after the time when flowering of that crop would have been expected.

11. A method according to claim 1 wherein the gibberellin is applied from 2 to 8 weeks after fruit bloom.

12. A method according to any preceding claim wherein the gibberellin is applied at a rate of from 1 to 500 µg per spur or short shoot.

13. A method according to claim 1 wherein gibberellin is applied at a rate of from 3 to 300 µg per spur or short shoot.

* * * * *